United States Patent [19]

Bennion et al.

[11] Patent Number: 4,499,269
[45] Date of Patent: Feb. 12, 1985

[54] FUSED 1,3,5-TRIAZINES

[75] Inventor: Colin Bennion, Loughborough, England; David Robinson, Shepshed, England

[73] Assignee: Fisons plc, Ipswich, England

[21] Appl. No.: 486,795

[22] Filed: Apr. 20, 1983

[30] Foreign Application Priority Data

Apr. 30, 1982 [GB] United Kingdom ................ 8212654

[51] Int. Cl.³ ................ C07D 513/04; C07D 498/04; C07D 487/04
[52] U.S. Cl. ..................................... 544/198; 544/209
[58] Field of Search ............... 544/208, 209, 197, 198

[56] References Cited

U.S. PATENT DOCUMENTS 3,309,366 3/1967 Schlapfer et al. ................ 260/249.6

Primary Examiner—John M. Ford
Attorney, Agent, or Firm—Marshall, O'Toole, Gerstein, Murray & Bicknell

[57] ABSTRACT

There are described compounds of formula I,

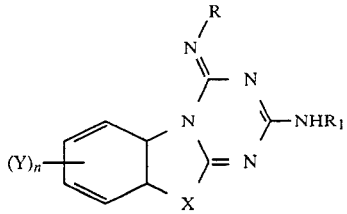

in which
X is O, S or N—$R_7$,
each Y, which may be the same or different, is H, OH, alkyl C1–C8, alkoxy C1–C8 or halogen,
n is an integer from 1 to 4 inclusive,
R and $R_1$, which may be the same or different, are each H; alkanoyl C2–C8 or a group $R_4$ in which $R_4$ is alkyl C1–C8 optionally substituted by phenyl; or is cycloalkyl C5 or C6; or is a group of formula XVI,

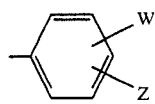

in which
W and Z, which may be the same or different, are each H, OH, alkoxy C1–C8, phenyl-alkoxy C7 to C10, alkyl C1–C8, halogen, —$NR_2R_3$, —$COOR_2$, $NO_2$, alkanoyloxy C2–C8, or —$OCH_2CH_2NR_2R_3$, and
$R_2$, $R_3$ and $R_7$, which may be the same or different, are each H or alkyl C1–C8,
provided that when X is N—$R_7$ and R is H, then $R_1$ is not (a) H when any Y groups are H, alkyl C1–C8, alkoxy C1–C8 or halogen, or (b) unsubstituted phenyl when all Y groups are H,
and pharmaceutically acceptable salts thereof.

There is also described the formulation and use of the compounds as pharmaceuticals, and processes for their production.

34 Claims, No Drawings

FUSED 1,3,5-TRIAZINES

This invention relates to new compounds, methods for their preparation and compositions containing them.

According to the invention we provide compounds of formula I,

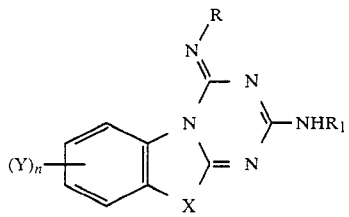   I in which
X is O, S or N-$R_7$,
each Y, which may be the same or different, is H, OH, alkyl C1–C8, alkoxy C1–C8 or halogen,
n is an integer from 1 to 4 inclusive,
R and $R_1$, which may be the same or different, are each H; alkanoyl C2–C8 or a group $R_4$ in which $R_4$ is alkyl C1–C8 optionally substituted by phenyl; or is cycloalkyl C5 or C6; or is a group of formula XVI,

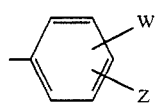   XVI in which
W and Z, which may be the same or different, are each H, OH, alkoxy C1–C8, phenyl-alkoxy C7 to C10, alkyl C1–C8, halogen, —$NR_2R_3$, —$COOR_2$, $NO_2$, alkanoyloxy C2–C8, or —$OCH_2CH_2NR_2R_3$, and
$R_2$, $R_3$ and $R_7$, which may be the same or different, are each H or alkyl C1–C8,
provided that when X is N-$R_7$ and R is H, then $R_1$ is not (a) H when any Y groups are H, alkyl C1–C8, alkoxy C1–C8 or halogen, or (b) unsubstituted phenyl when all Y groups are H,
and pharmaceutically acceptable salts thereof.

According to the invention we also provide the compounds of formula I without provisos, and in particular without proviso (b), and pharmaceutically acceptable acid addition salts thereof, for use as pharmaceuticals.

According to the invention we further provide a process for the production of a compound of formula I, or a pharmaceutically acceptable salt thereof, which comprises (a) producing a compound of formula I in which one of R and $R_1$ is hydrogen and the other is a group $R_4$, by reaction of a compound of formula II, NC—N=CS($R_x$)—$NHR_4$   II or a salt thereof,
in which
$R_x$ is hydrogen or alkyl, and $R_4$ is as defined above, with a compound of formula III,

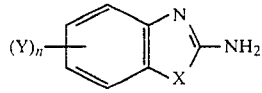   III in which X, Y and n are defined as above, (b) producing a compound of formula I in which R is a group $R_4x$, and $R_1$ is hydrogen or a group $R_4x$, in which $R_4x$ has the same meaning as $R_4$ save that W and Z do not represent —$NHR_3$, —$OCH_2CH_2NHR_3$, —OH or —COOH by reaction of a compound of formula IV, $R_4x$—N=C(Hal)$_2$   IV in which
$R_4x$ is defined as above, and Hal is halogen, with a compound of formula V,

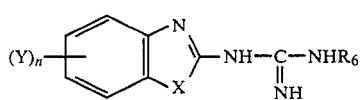   V in which X, Y and n are defined as above, and $R_6$ is hydrogen or a group $R_4x$, (c) producing a compound of formula I in which $R_1$ is a group $R_4$ and R is hydrogen, by cyclisation of a compound of formula VI,

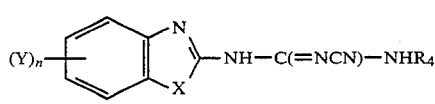   VI in which X, Y, n and $R_4$ are as defined above, (d) producing a compound of formula I in which at least one of R and $R_1$ is alkanoyl C2 to C8 or at least one of W and Z is alkanoyloxy C2 to C8, by selective C2 to C8 alkanoylation of a corresponding compound of formula I in which at least one of R and $R_1$ is hydrogen, or at least one of W and Z is —OH, (e) producing a compound of formula I in which R is a group $R_4x$ and $R_1$ is $R_6$ by cyclisation of a compound of formula VII or VIII,

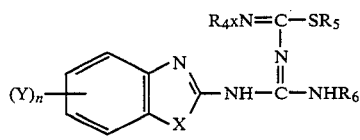   VII

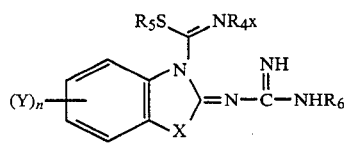   VIII in which X, Y, n, $R_4x$ and $R_6$ are as defined above, and $R_5$ is alkyl C1–C8, (f) producing a compound of formula 1 in which W is hydrogen and Z is —OH, by selective cleavage of a corresponding compound of formula I in which W is hydrogen and Z is alkoxy or phenylalkoxy, or (g) producing a compound of formula I in which R and R₁ are both hydrogen, by reaction of a compound of formula IX,

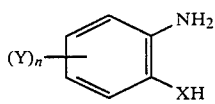   IX in which X, Y and n are defined as above, with a compound of formula XVII, (R₅S)₂C=N—C(NH₂)=N—CN    XVII in which R₅ is as defined above,
and if desired or necessary converting the resulting compound of formula I to a pharmaceutically acceptable salt thereof, or vice versa.

Process (a) may be carried out in a solvent which is inert under the reaction conditions, e.g. tetrahydrofuran, at temperatures ranging from 0° C. to the reflux temperature of the solvent e.g. 70° C. The salt of the compound of formula II is preferably an alkali metal, e.g. the sodium, salt thereof. The reaction is preferably carried out in the presence of a heavy metal salt, e.g. mercuric chloride. Excess mercuric salts can be conveniently removed by the addition of H₂S or by recrystallisation.

Process (b) may be carried out in a solvent which is inert under the reaction conditions, e.g. tetrahydrofuran, and preferably in the presence of a base, e.g. diisopropylethylamine. The reaction may be carried out at temperatures ranging from about 0° C. to the reflux temperature of the solvent, e.g. 70° C.

The cyclisation of process (c) is preferably carried out in the presence of a mild acid, e.g. silica gel. The reaction may be carried out in a solvent which is inert under the reaction conditions, e.g. a mixture of water and tetrahydrofuran. The reaction may be carried out at a temperature of from about 0° to 100° C., e.g. at about 25° C.

The alkanoylation of process (d) may be carried out under amine or hydroxyl alkanoylation conditions as appropriate, for example using an alkanoylating agent, e.g. an acid anhydride, in the presence of a base, e.g. pyridine, at a temperature of from about 25° to 125° C., preferably at about 100° C.

The cyclisation of process (e) may be carried out in a solvent which is inert under the reaction conditions, e.g. dimethylformamide. The reaction may be carried out at a temperature of from about 0° to 100° C., e.g. at 25° C.

The selective cleavage of process (f) may be carried out under conditions which will not adversely affect the rest of the molecule. Thus, for example, the cleavage may be solvolysis, e.g., hydrolysis, and may be carried out under acidic conditions, using for example hydrogen bromide in acetic acid. The reaction may be carried out at a temperature of from 0° to 100° C., preferably at about 30° C. We prefer to use a starting material in which Z is phenylalkoxy, e.g. benzyloxy.

Process (g) may be carried out in a solvent which is inert under the reaction conditions, e.g. ethanol. The reaction may be carried out at from 0° C. to the boiling point of the solvent, e.g. 80° C. and is preferably carried out at about 25° C.

The starting materials for processes (a) to (g) above are either known or may be made from known compounds by processes disclosed in the Examples or by processes analogous thereto, e.g. the processes described below. Alternatively the starting materials may be made from known materials using techniques which are known per se.

The compounds of formula VI may be made by reaction, e.g. in dioxan at from 0° C. to 100° C., of a compound of formula X,

ICH₂—O—CO—C(CH₃)₃    X with a compound of formula III, to yield a compound of formula XI,

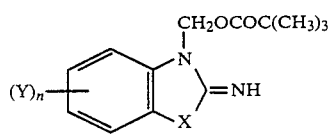   XI in which X, Y and n are as defined above,
reaction of the compound of formula XI with a compound of formula II, or a sodium salt thereof, e.g. under similar reaction conditions to those set out above for process (a),
and base, e.g. sodium hydroxide, hydrolysis of the resulting compound of formula XII,

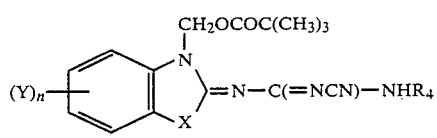   XII in which X, Y, n and R₄ are as defined above.

The compounds of formulae VII and VIII may be made by reaction of a compound of formula V with a compound R₄xNCS in which R₄x is as defined above, e.g. in the presence of a base, such as sodium hydride, to produce a compound of formula XIII or XIV,

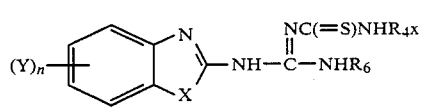   XIII

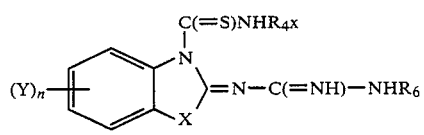   XIV in which X, Y, n, R₄x and R₆ are as defined above, followed by reaction of the compound of formula XIII or XIV, or the sodium salts thereof, with an alkyl halide, e.g. iodide, R₅Hal, to produce a compound of formula VII or VIII.

The starting materials for process (f) may be made by other processes of the invention.

The compounds of formulae II, III, IV, V, IX, X, XVII and R₄xNCS are either known or may be made from known compounds using conventional techniques known per se.

Many of the starting materials and intermediates for the processes described above may exist in tautomeric forms other than those indicated. Where appropriate these other tautomeric forms, which will be readily recognised by the skilled chemist, are included as equivalents of the specific forms illustrated. Compounds of formulae II, VI, VII, VIII, XIII and XVII may also exist as syn and anti isomers.

The compounds of formula I, and the intermediates therefore, may be recovered from their reaction mixtures using conventional techniques which are known per se.

Pharmaceutically acceptable salts of the compounds of formula I include salts with pharmaceutically acceptable organic or inorganic anions, e.g. the chloride, sulphate, maleate or tartrate anions, or, when W or Z is —COOH, or —OH salts with pharmaceutically acceptable organic or inorganic cations, e.g. an alkali metal cation such as sodium.

The compounds of formula I, and the pharmaceutically acceptable salts thereof, are useful because they possess pharmacological activity in animals; in particular they are useful because they possess immuno-regulant activity, e.g. in the tests set out in Examples A, B or C. Thus the new compounds are indicated for use in the treatment of auto-allergic diseases including systemic lupus erythematosus, rheumatoid arthritis, Reiter's syndrome, multiple sclerosis, myasthenia gravis, Goodpastures disease, rheumatic fever, acute hepatitis, primary biliary cirrhosis, autoimmune haemolytic anaemia, idiopathic thrombocytopenia purpura, sclerodermas, hyroiditis, orchitis, uveitis and Addison's disease; dermatitis, e.g. atopic, contact (both direct and allergic), seborrhoeic, numular, statis or neuro dermatitis; psoriasis; skin malignancies; eczema, e.g. infantile eczema; in the maintenance of allografts, e.g. renal allografts, and in the treatment of tumours, for example lymphoproliferative neoplasias such as myeloma, lymphomas and leukaemias.

For the above mentioned uses the dosage administered will, of course, vary with the compound employed, the mode of administration and the treatment desired. However, in general, satisfactory results are obtained when the compounds are administered at a dosage of from 10 to 200 mg per kg of animal body weight in the tests set out in Examples A and B. For man, the indicated total daily dosage is in the range of from 10 mg to 1000 mg and preferably from 50 mg to 500 mg which may be administered in divided doses from 1 to 6 times a day or in sustained release form. Thus unit dosage forms suitable for administration, e.g. oesophageally, comprise from 2 mg to 500 mg, and preferably 10 mg to 500 mg of the compound preferably admixed with a solid or liquid pharmaceutically acceptable diluent, carrier or adjuvant.

For topical applications, dosages are difficult to control, but in general a dosage of from about 0.1 to 10 mg, and preferably of from 2 to 5 mg, per 16 square cms of skin is indicated.

In addition to the above uses the compounds of the invention may be used as bactericides.

We prefer X to be S. Each Y group preferably contains up to and including 4 carbon atoms and is preferably in the 8-position. Thus specific groups Y which may be mentioned include methyl, propoxy, hydroxy, chloro, and preferably methoxy. We prefer there to be 1 or 2 substituents Y. Specific groups R which may be mentioned include hydrogen, phenyl, butyl, methyl, benzyloxyphenyl, benzyl, dimethylaminophenyl, mono- or di-halo- (e.g. chloro-) phenyl, methoxyphenyl, methylphenyl, carboxyphenyl, ethoxycarbonylphenyl, cyclohexyl, diethylaminoethoxyphenyl and hydroxyphenyl. We thus prefer R to comprise a phenyl group.

When W and/or Z comprises an alkyl or alkoxyl group we prefer that alkyl or alkoxy group to contain from 1 to 4, e.g. 1 or 2, carbon atoms. When W and/or Z is halogen it is preferably chlorine. Specific groups $R_1$ which may be mentioned include hydrogen, phenyl and alkanoyl C2 to 4, e.g. acetyl.

We particularly prefer compounds in which X is S, Y is alkoxy, e.g. methoxy (preferably in the 8-position) n is 1, $R_1$ is hydrogen and R is phenyl optionally substituted by one or two chlorine atoms (e.g. 4-chloro or 3,4-dichloro) or by one —OCH$_2$CH$_2$N(C$_2$H$_5$)$_2$ group, e.g. in the 4-position.

According to our invention we also provide a pharmaceutical composition comprising (preferably less than 80%, and more preferably less than 50% by weight) of a compound of formula I without the provisos, or a pharmaceutically acceptable salt thereof, in combination with a pharmaceutically acceptable adjuvant, diluent or carrier. Examples of suitable adjuvants, diluents or carriers are: for tablets, capsules and dragées; microcrystalline cellulose, calcium phosphate, diatomaceous earth, a sugar such as lactose, dextrose or mannitol, talc, stearic acid, starch, sodium bicarbonate and/or gelatin; for suppositories, natural or hardened oils or waxes; and for inhalation compositions, coarse lactose. Examples of suitable formulations for topical administration include sprays, paints, creams, emulsions, oils, ointments, lotions, solutions, etc. each of which may comprise suitable excipients, adjuvants or carriers. The compound of formula I, or the pharmaceutically acceptable salt thereof, preferably is in the form having a mass median diameter of from 0.01 to 10 microns. The compositions may also contain suitable preserving, stabilising and wetting agents, solubilisers, sweetening and colouring agents and flavourings. The compositions may, if desired, be formulated in sustained release form or for topical application. We prefer compositions which are designed to be administered topically, e.g. for the treatment of contact sensitivity, or to be taken oesophageally and to release their contents in the gastrointestinal tract.

The compounds of formula I may exist in a number of tautomeric forms and these forms are included within the scope of the present invention.

The compounds of formula I may also exist as syn and anti isomers, or a mixture thereof, and these isomers may be separated by conventional methods known per se.

Tautomerism/isomerism within the compounds of the invention is illustrated by the compound of Example 1:

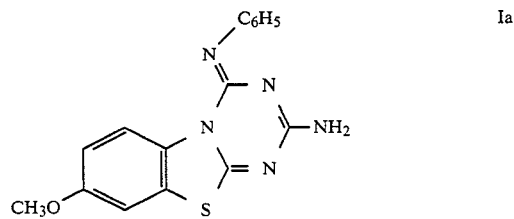

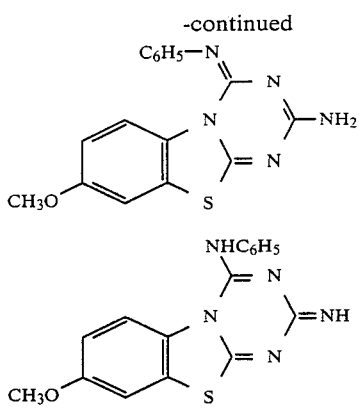

Form Ia is preferred.

For compounds of formula I in which X is NH a further form is:

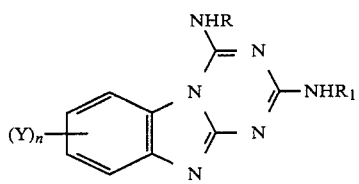

Certain of the compounds of formula I may also form solvates or hydrates, e.g. the hydrochloride of the compound of Example 1 forms a monohydrate. The compounds of formula I may also form polymorphs. In general we prefer to use the most stable tautomer, isomer, hydrate or polymorph at room temperature for use in pharmaceutical formulations.

The invention is illustrated, but in no way limited by the following examples in which the temperatures are in °C.

EXAMPLE 1

(a)

2-Amino-8-methoxy-4-phenylimino-4H-1,3,5-triazino[2,1-b]benzothiazole

A solution of 2-amino-6-methoxy benzothiazole (9.0 g) in dry tetrahydrofuran was treated with the sodium salt of N-cyano-N'-phenyl thiourea (5.0 g) and finely powdered mercuric chloride (6.75 g) and the mixture stirred at room temperature for 24 hours.

The insoluble solids were removed by filtration and the resulting clear solution evaporated to dryness. Trituration of the residue with methanol yielded the crude product which was purified by dissolution in tetrahydrofuran, filtration and evaporation. Yield 1.4 g, m.p. >280°.

Found: C 59.27, H 3.80, N 21.37, S 9.55%, $C_{16}H_{13}N_5OS$

Requires: C 59.44, H 4.02, N 21.67, S 9.91%.

The mass spectrum showed M+323 (MW323)

(b)

2-Amino-8-methoxy-4-phenylimino-4H-1,3,5-triazino[2,1-b]benzothiazole hydrochloride A solution of the product of part (a) (2.0 g) in tetrahydrofuran (500 ml) was treated with 1N hydrochloric acid (6.18 ml) at room temperature. The resulting solid was collected by filtration and dried to give the product monohydrate (1.55 g) as white crystals, m.p.>270°.

Found: C 50.93; H 4.23; N 18.34; Cl 9.79;S 8.85%, $C_{16}H_{14}ClN_5OS \cdot H_2O$, Requires: C 50.86; H 4.27; N 18.53; Cl 9.38; S 8.48%.

EXAMPLE 2

2-Amino-4-phenylimino-4H-1,3,5-triazino[2,1-b]benzothiazole

A mixture of 2-aminobenzothiazole (21.82 g), the sodium salt of N-cyano-N'-phenyl thiourea (29 g) and mercuric chloride (39.15 g) in dry tetrahydrofuran (1.5 l) was stirred at room temperature for three days, filtered through a filter aid and the filtrate evaporated to give a yellow solid (44 g). Trituration of the residue with ethanol gave a solid which was suspended in tetrahydrofuran (800 ml) and saturated with hydrogen sulphide. The black precipitate was removed by filtration through a filter aid, and the filtrate evaporated to dryness. Trituration of the residue with ethanol followed by recrystallisation of the resulting solid from dimethylformamide gave the title compound as white crystals (1.82 g) mp>250°.

The Mass Spectrum showed M+293 (Mw 293).

The infrared spectrum showed the absence of a nitrile absorption.

Found: C 61.30%; H 3.85%; N 23.58%; S 11.15%, $C_{15}H_{11}N_5S$

Requires: C 61.42%; H 3.78%; N 23.87%; S 10.93%.

EXAMPLE 3

2-Amino-4-phenylimino-4H-1,3,5-triazino[1,2-a]benzimidazole hydrochloride (a)

2-Amino-4-phenylimino-4H-1,3,5-triazino[1,2-a]benzimidazole

A suspension of 2-aminobenzimidazole (10.0 g) and the sodium salt of N-cyano-N'-phenyl thiourea (7.5 g) was stirred at room temperature for 30 minutes. Mercuric chloride (10.2 g) was added and stirring continued for 16 h. The mixture was filtered and the filtrate evaporated to a gum. A solution of the gum in methanol soon yielded a solid (3.25 g). The solid was collected, suspended in tetrahydrofuran and hydrogen sulphide added until no further black precipitate formed. The mixture was filtered and the filtrate evaporated to give a yellow solid which showed several components on thin layer chromatography. The components were separated on a column of silica gel to give the sub-title compound as white crystals (1.22 g) mp, 271°-3°.

Found: C 64.81, H 4.39, N 29.97%, $C_{15}H_{12}N_6$,

Requires: C 65.22, H 4.35, N 30.43%.

(b)

2-Amino-4-phenylimino-4H-1,3,5-triazino[1,2-a]benzimidazole hydrochloride

The product from part (a) (276 mg) in water (50 ml) was warmed with 1M hydrochloric acid (5 ml) to solution and then evaporated to one half volume whereupon a solid (240 mg) crystallised. Recrystallisation from ethanol gave the title compound as the ethanolate. mp 266°-8°.

Found: C 56.81, H 5.39, N 23.70, Cl 9.8% $C_{15}H_{12}N_6 \cdot HCl \cdot C_2H_5OH$, Requires: C 56.90, H 5.30, N 23.44, Cl 9.9%.

EXAMPLE 4

4-Imino-2-phenylamino-4H-1,3,5-triazino[1,2-a]benzimidazole

Further elution of the chromatography column described in Example 3 (a) yielded a more polar compound as a white solid which was recrystallised from dimethyl formamide. The title product (0.3 g) was obtained as white crystals, mp>300° which retained a small amount of solvent (n.m.r. and thermogravimetric analysis indicate the presence of 9.3% dimethylformamide).

Found: C 63.82, H 5.01, N 29.45%,
$C_{15}H_{12}N_6 + 9.3\%$ HCONMe$_2$,
Requires: C 63.74, H 4.84, N 29.38%.

EXAMPLE 5

2-Amino-8-methoxy-4-cyclohexylimino-4H-1,3,5-triazino[2,1-b]benzothiazole

A solution of 2-amino-6-methoxy benzothiazole (9.0 g), methyl N-cyano-N'-cyclohexylcarbamidothioate (10.0 g) and mercuric chloride (13.8 g) in a mixture of dry tetrahydrofuran (300 ml) and dimethylformamide (100 ml) was stirred at room temperature for seven days. The insoluble residues were removed by filtration and the filtrate evaporated to a gum. A solution of the gum in a mixture of ethyl acetate and tetrahydrofuran was washed with sodium hydroxide solution and water. Hydrogen sulphide was passed through the dried organic phase until precipitation of black solid was complete. The solution was filtered through a filter aid and the filtrate evaporated to a solid. Recrystallisation of the residue from ethanol yielded the title compound as a white crystalline solid (3.5 g), mp 228°–30°.

The Mass Spectrum showed M+329 (Mw 329).
Found: C58.41 H5.80 N21.14 S10.02%,
$C_{16}H_{19}N_5OS$,
Requires: C58.36 H5.78 N21.28 S29.73%.

EXAMPLE 6

2-Amino-4-phenylimino-4H-1,3,5-triazino[2,1-b]benzothiazole

Phenyl isocyanide dichloride (0.18 g) in dry tetrahydrofuran (5 ml) was added to a stirred solution of 2-benzothiazolylguanidine (0.2 g) and diisopropylethylamine (0.27 g) in dry tetrahydrofuran (10 ml). The mixture was refluxed for sixteen days and on cooling the title compound was obtained as a white crystalline solid (23 mg) mp>250°.

The product was identical (mass spectrum, nmr spectrum, thin layer chromatography) to the product of Example 2.

EXAMPLE 7

4-Imino-8-methoxy-2-phenylamino-4H-1,3,5-triazino[2,1-b]benzothiazole

(a)
[6-Methoxy-2-imino-3(2H)-benzothiazolyl]-methyl-2,2-dimethyl-propanoate hydroiodide A solution of 2-amino-6-methoxy benzothiazole (8.5 g) and iodomethyl pivalate (11.5 g) in dry dioxan (120 ml) was stored at room temperature for 7 days. The resulting solid was collected and dried to give the sub-title product (14 g), mp 191°–3° as a hemi-solvate with dioxan (n.m.r.).

(b)
[6-Methoxy-2-(phenylamino)-(cyanoimino)methyl)-imino-3(2H)-benzothiazolyl]-methyl 2,2-dimethyl-propanoate A suspension of the hydroiodide salt (4.0 g) from step (a) was stirred with ethyl acetate (200 ml) and 0.5M sodium hydroxide solution for 0.5 hours. The organic phase was separated, washed with water, dried (Na$_2$SO$_4$) and evaporated to a clear orange gum. A solution of the gum in dry tetrahydrofuran (100 ml) was treated with the sodium salt of N-cyano-N'-phenyl thiourea (2.0 g) and mercuric chloride (2.7 g) and the resulting suspension stirred at room temperature for 24 hours. The mixture was filtered and hydrogen sulphide added to the filtrate until precipitation of black solid was complete. The mixture was filtered and the filtrate evaporated to a semisolid residue. Trituration with methanol gave a crystalline solid (1.41 g), mp 257°–60°.

Found C 60.41, H 5.31, N 15.86, S 7.50%,
$C_{22}H_{23}N_5O_3S$,
Requires C 60.41, H 5.26, N 16.02, S 7.32%.

(c)
N-Cyano-N'-(6-methoxy-2-benzothiazolyl)-N''-phenyl guanidine

A solution of the product of step (b) (1.6 g) in tetrahydrofuran (200 ml) and 1M sodium hydroxide solution (100 ml) was stirred vigorously for 4 hours. The mixture was separated, the organic phase diluted with ethyl acetate (200 ml), and washed with brine, dried and evaporated to give the sub-title product as a white solid (1.2 g), mp 224°–5°.

The Mass Spectrum showed M+323 (mw323).
The Infra Red Spectrum showed a strong band at 2180 cm$^{-1}$ (N—C≡N).

(d)
4-Imino-8-methoxy-2-phenylamino-4H-1,3,5-triazino[2,1-b]benzothiazole Silica gel (chromatography grade) (20 g) was added to a solution of the product of step (c) (1.2 g) in tetrahydrofuran (50 ml) and the suspension stirred for 1 hour. The mixture was filtered, the filtrate evaporated to dryness and the residue triturated with methanol to yield a white solid. Recrystallisation of the solid from ethanol yielded the title compound (1.2 g) as white crystals, mp 225°–6°.

Found: C 59.82, H 4.27, N 21.59, S 10.10%.
$C_{16}H_{13}N_5OS$,
Requires: C 59.44, H 4.02, N 21.67, S 9.91%

EXAMPLE 8

2-Acetylamino-8-methoxy-4-phenylimino-4H-1,3,5-triazino[2,1-b]benzothiazole

2-Amino-8-methoxy-4-phenylimino-4H-1,3,5-triazino[2,1-b]benzothiazole (0.3 g) and acetic anhydride (0.14 g) in dry pyridine (15 mls) were heated at 100° for 24 hours. After cooling to room temperature, methanol (5 mls) was added, the solution was stirred for 1 hour and the solvents were removed in vacuo. The residue was dissolved in chloroform, the solution washed with water, brine, dried (Na$_2$SO$_4$) and evaporated in vacuo to give a yellow solid (0.27 g). Purification by chromatography (silica gel, chloroform) gave the title compound as pale yellow crystals (0.18 g), mp 248°–29°.

The Mass Spectrum showed M+365 (Mw 365)
Found: C58.98 H4.18 N19.00 S8.99%,
C$_{18}$H$_{15}$N$_5$O$_2$S
Requires: C59.17 H4.14 N19.17 S8.77%.

EXAMPLE 9

2-Amino-4-[4-(2-diethylaminoethoxy)phenyl]imino-8-methoxy-4H-1,3,5-triazino[2,1-b]benzothiazole

(a) Methyl N-(6-methoxybenzothiazol-2-yl)carbamidothioate hydroiodide

Methyl iodide (2.8 ml) was added to a suspension of N-(6-methoxybenzothiazol-2-yl)thiourea (9.4 g) in isopropanol and the mixture heated at reflux for 16 h. The resulting precipitate was collected by filtration and dried to give the sub-title product (5.2 g) as fluffy needles, mp 199° (dec.).
The Mass Spectrum showed M+ 253 (Mw 253).

(b) N-(6-Methoxybenzothiazol-2-yl)guanidine

A suspension of the product from step (a) (14 g) in methanolic ammonia was heated in a sealed vessel at 100° for 16 h. The resulting mixture was cooled, evaporated to dryness and the residue stirred with 10% sodium hydroxide solution (200 ml) for 1 h. The solid was collected by filtration and recrystallised from a mixture of methanol, ether and petroleum ether (b.p. 40°-60°). The sub-title product (2.0 g) was isolated as white crystals, mp 253° (dec.).
The Mass Spectrum showed M+ 222 (Mw 222).

(c) 2-Amino-4-[4-(2-diethylaminoethoxy)phenyl]imino-8-methoxy-4H-1,3,5-triazino[2,1-b]benzothiazole 6-Methoxybenzothiazol-2-ylguanidine (0.2 g) was added to a suspension of sodium hydride (0.022 g=0.044 g of 50% dispersion in oil) in anhydrous dimethylformamide (20 mls) and the resulting mixture was stirred at room temperature for 15 mins. 4-(2-Diethylaminoethoxy)phenylisothiocyanate (0.23 g) was added followed, after 2.5 hrs, by methyl iodide (0.14 g) and the mixture stirred for a further 18 hrs. Water was added to precipitate a yellow solid which was collected by filtration, washed with ethanol and dissolved in ethyl acetate. The ethyl acetate solution was dried over anhydrous sodium sulphate and evaporated to give a yellow solid (0.33 g). Recrystallisation of the residue from ethyl acetate gave the desired product as pale yellow crystals (0.08 g) mp 189.5°-191°.
The Mass Spectrum showed M+438 (Mw 438).
Found: C 60.25%; H 6.01%; N 19.23%; S 7.28%.
C$_{22}$H$_{26}$N$_6$O$_2$S,
Requires: C 60.25%; H 6.00%; N 19.16%; S 7.31%.

EXAMPLE 10

8-Methoxy-2-phenylamino-4-phenylimino-4H-1,3,5-triazino[2,1-b]benzothiazole

(a) Methyl N-(6-methoxybenzothiazol-2-yl)-N'-phenylcarbamidothioate hydroiodide A mixture of N-(6-methoxybenzothiazol-2-yl)-N'-phenyl thiourea (10.0 g) and methyl iodide (5.0 g) in isopropanol (500 ml) was heated at reflux for 2 h. A further portion of methyl iodide (2.0 g) was added and heating continued for a further hour. The mixture was cooled and the resulting solid collected. The sub-title product (9.0 g) had m.p. 178°-80°.

(b) N-(6-Methoxybenzothiazol-2-yl)-N'-phenyl guanidine hydrochloride

A suspension of the product from part (a) (2.0 g) in ethanolic ammonia (80 ml) was heated at 100° for 16 h. The mixture was cooled, evaporated to a gum and a solution of the residue in ethanol treated with excess ethanolic hydrogen chloride. Removal of solvents by evaporation yielded an oil which crystallised on trituration with ether. Recrystallisation from propanol yielded the sub-title product (1.0 g) as a white solid, m.p. 193°-6°.

(c) 8-Methoxy-2-phenylamino-4-phenylimino-4H-1,3,5-triazino[2,1-b]benzothiazole A suspension of the product from part (b) (2.0 g) in a mixture of sodium hydroxide solution (1N) and ethyl acetate (200 ml) was stirred until solution was obtained. The organic phase was removed, washed with water, dried and evaporated to a gum. A solution of the gum in dry dimethyl formamide (20 ml) was added to a stirred suspension of sodium hydride (300 mg of a 50% dispersion in oil) in the same solvent (20 ml) and stirring was continued for 1 h. A solution of phenylisothiocyanate (0.72 g) in dry dimethylformamide was added at room temperature and stirring continued for a further 2 h. Methyl iodide (0.7 g) was added and the reaction mixture allowed to stand at room temperature for 16 h. Addition of water (100 ml) resulted in the precipitation of a waxy solid which was collected and crystallised from acetonitrile to give the title compound as a pale cream crystals (400 mg), mp 213°-4°.
The Mass Spectrum showed M+399 (M.w. 399).
Found: C 66.43; H 4.46; N 17.06; S 8.09%,
C$_{22}$H$_{17}$N$_5$OS
Requires: C 66.17; H 4.26; N 17.54; S 8.02%.

EXAMPLE 11

2-Amino-4-(4-hydroxyphenyl)imino-8-methoxy-4H-1,3,5-triazino[2,1-b]benzothiazole The compound of Example 15 (4.1 g) was dissolved in glacial acetic acid (100 ml) and 45% hydrogen bromide/acetic acid (50 ml) was added. After stirring for 30 mins, the viscous mass was poured into water, neutralised with 10% sodium carbonate solution and the resulting precipitate collected by filtration. The solid was washed with ethanol to give the title compound as pale yellow crystals (2.94 g).
Recrystallisation from aqueous dimethylformamide (200 ml) gave the product as a white solid (0.88 g), mp>255°.
Found: C 56.23; H 4.06; N 20.51; S 9.73%
C$_{16}$H$_{13}$N$_5$O$_2$S
Requires: C 56.63; H 3.86; N 20.64; S 9.45%.
The Mass Spectrum showed M+339 (M.Wt. 339).

EXAMPLE 12

2-Amino-4-imino-4H-1,3,5-triazino[2,1-b]benzothiazole

A mixture of 2-aminothiophenol (0.3 ml) and dimethyl (amino) (cyanoimino)methylcarbonimidodithioate (0.5 g) in ethanol (20 ml) was stirred at room termperature for 18 hrs and then heated under reflux for 4 hrs. After cooling, the white precipitate was collected by filtration and recrystallised from ethanol/tetrahydrofuran (30 ml; 5:1) to give the product as a white solid. Recrystallisation from ethyl acetate/charcoal gave the product as white crystals (0.07 g) mp>260°.

Found: C 49.89%; H 3.42%; N 31.96%, $C_9H_7N_5S$.

Requires: C 49.76%; H 3.25%; N 32.24%.

The Mass Spectrum showed $M^+$ 217 (M.w. 217)

EXAMPLES 13-30

The following compounds were synthesised using appropriate starting materials and the processes indicated.

Examples 13-29

| Example No | X | Y | R | $R_1$ | Process Example No | Melting Point | Analysis | | C | H | N | S | Cl |
|---|---|---|---|---|---|---|---|---|---|---|---|---|---|
| 13 | S | 8-CH₃ | phenyl | H | (a) Ex 1 | >260° | $C_{16}H_{13}N_5S$ | Found Req. | 62.14 62.54 | 4.38 4.23 | 22.52 22.80 | 10.41% 10.42% | |
| 2-Amino-8-methyl-4-phenylimino-4H—1,3,5-triazino[2,1-b] benzothiazole | | | | | | | | | | | | | |
| 14 | S | 8-OCH₃ | t-butyl | H | (a) Ex 5 | 213° | $C_{14}N_{17}N_5OS$ | Found Req. | 55.83 55.43 | 5.65 5.65 | 23.37 23.08 | 10.26% 10.57% | |
| 2-Amino-4-(1,1-dimethylethyl)imino-8-methoxy-4H—1,3,5-triazino[2,1-b] benzothiazole | | | | | | | | | | | | | |
| 15 | S | 8-OCH₃ | 4-benzyloxy phenyl | H | (a) Ex 5 | 232-3° | $C_{23}H_{19}N_5O_2S$ | Found Reg. | 64.34 64.32 | 4.63 4.46 | 16.17 16.31 | 7.19% 7.46% | |
| 2-Amino-8-methoxy-4-[4-(phenylmethoxy)phenyl]imino-4H—1,3,5-triazino[2,1-b] benzothiazole | | | | | | | | | | | | | |
| 16 | S | 8-OCH₃ | benzyl | H | (a) Ex 5 | 182-5° | $C_{17}H_{15}N_5OS$. 1.5% H₂O | Found Reg. | 59.49 59.82 | 20.20 20.52 | 4.43 4.42 | 9.31% 9.20% | |
| 2-Amino-8-methoxy-4-phenylmethylimino-4H—1,3,5-triazino[2,1-b] benzothiazole | | | | | | | | | | | | | |
| 17 | S | 8-OCH₃ | 4-(dimethyl amino)phenyl | H | (a) Ex 2 | 228° (dec) | $C_{18}H_{18}N_6OS$ HCl 5% H₂O | Found Reg. | 50.86 50.98 | 4.58 4.48 | 19.82 19.83 | 7.80 7.60 | 8.51% 8.38% |
| 2-Amino-4-[4-N,N—dimethylamino)phenyl[imino-8-methoxy-4H—1,3,5-triazino[2,1-b] benzothiazole | | | | | | | | | | | | | |
| 18 | S | 8-iso-propoxy | phenyl | H | (a) Ex 2 | 269-270° | $C_{18}H_{17}N_5OS$ | Found Reg. | 61.30 61.52 | 4.84 4.88 | 19.95 19.93 | 9.31% 9.12% | |
| 2-Amino-8-(1-methylethoxy)-4-phenylimino-4H—1,3,5-triazino[2,1-b] benzothiazole | | | | | | | | | | | | | |
| 19 | S | 8-OH | phenyl | H | (a) Ex 2 | >265° | $C_{15}H_{11}N_5OS$ 4% tetrahydro-furan | Found Reg. | 58.24 58.57 | 3.91 3.88 | 21.65 21.73 | 10.20% 9.95% | |
| 2-Amino-8-hydroxy-4-phenylimino-4H—1,3,5-triazino[2,1-b] benzothiazole | | | | | | | | | | | | | |
| 20 | S | 8-OCH₃ | 2,6-dichloro phenyl | H | (a) Ex 2 | >265° | $C_{16}H_{11}Cl_2N_5OS$ | Found Reg. | 49.05 48.99 | 2.88 2.83 | 17.99 17.85 | 8.22 8.17 | 18.03% 18.03% |
| 2-Amino-4-(2,6-dichlorophenyl)imino-8-methoxy 4H—1,3,5—triazino[2,1-b] benzothiazole | | | | | | | | | | | | | |
| 21 | S | 8-OCH₃ | 4-methoxy phenyl | H | (a) Ex 2 | 247-9° | $C_{17}H_{15}N_5O_2S$ | Found Reg. | 58.03 57.78 | 4.32 4.28 | 19.95 19.82 | 8.98% 9.07% | |
| 2-Amino-8-methoxy-4-(4-methoxyphenyl)-imino-4H—1,3,5-triazino[2,1-b] benzothiazole | | | | | | | | | | | | | |
| 22 | S | 8-OCH₃ | 3,4-dichloro-phenyl | H | (a) Ex 2 | >265° | $C_{16}H_{11}Cl_2N_5OS$ | Found Reg. | 48.65 48.99 | 2.83 2.83 | 17.55 17.85 | 8.27 8.17 | 18.48% 18.08% |
| 2-Amino-4-(3,4-dichlorophenyl)imino-8-methoxy-4H—1,3,5-triazino[2,1-b] benzothiazole | | | | | | | | | | | | | |
| 23 | S | 8-OCH₃ | 4-chloro-phenyl | H | (a) Ex 2 | 247-8° | $C_{16}H_{12}ClN_5OS$ | Found Reg. | 53.88 53.71 | 3.39 3.38 | 19.97 19.57 | 9.18 8.96 | 9.97% 9.91% |
| 2-Amino-4-(4-chlorophenyl)imino-8-methoxy-4H—1,3,5-triazino[2,1-b] benzothiazole | | | | | | | | | | | | | |
| 24 | S | 8-OCH₃ | 4-methyl phenyl | H | (a) Ex 2 | 244-6° | $C_{17}H_{15}N_5OS$ | Found Reg. | 60.47 60.52 | 4.62 4.48 | 20.56 20.76 | 9.25% 9.50% | |
| 2-Amino-8-methoxy-4-(4-methylphenyl)imino-4H—1,3,5-triazino[2,1-b] benzothiazole | | | | | | | | | | | | | |
| 25 | O | H | phenyl | H | (a) Ex 1 | 260° | $C_{15}H_{11}N_5O$ | Found Reg. | 64.71 64.97 | 4.07 4.00 | 25.23% 25.26% | | |
| 2-Amino-4-phenylimino-4H—1,3,5-triazino[2,1-b]-benzoxazole | | | | | | | | | | | | | |
| 26 | S | 8-Cl | phenyl | H | (a) Ex 1 | 288-9° | $C_{15}H_{10}ClN_5S$ | Found Reg. | 54.98 54.96 | 3.10 3.05 | 21.12 21.37 | 9.70 9.77 | 10.70% 10.84% |
| 2-Amino-8-chloro-4-phenylimino-4H—1,3,5-triazino[2,1-b] benzothiazole | | | | | | | | | | | | | |
| 27 | S | 8-OCH₃ | 4-carboxy phenyl | H | (a) Ex 5 | 246° (dec) | $C_{17}H_{13}N_5O_3S$ | Found Reg. | 54.83 55.59 | 3.48 3.54 | 18.38% 19.07% | | |
| 2-Amino-4-(4-carboxyphenyl)imino-8-methoxy-4H—1,3,5-triazino[2,1-b] benzothiazole | | | | | | | | | | | | | |
| 28 | S | 8-OCH₃ | 4-ethoxy carbonyl-phenyl | H | (a) Ex 2 | 236-8° | $C_{19}H_{17}N_5O_3S$ | Found Reg. | 57.32 57.72 | 4.32 4.30 | 17.43 17.72 | 8.37% 8.10% | |
| 2-Amino-4-(4-ethoxycarbonylphenyl)imino-8-methoxy-4H—1,3,5-triazino [2,1-b] benzothiazole | | | | | | | | | | | | | |
| 29 | S | 7,8-di-CH₃ | phenyl | H | (a) Ex 2 | >260° | $C_{17}H_{15}N_5S$ | Found Reg. | 63.40 63.53 | 4.56 4.70 | 21.66 21.79 | 9.99% 9.95% | |
| 2-Amino-8-7,-dimethyl-4-phenylimino-4H— | | | | | | | | | | | | | |

-continued

Examples 13–29

| Example No | X | Y | R | R₁ | Process Example No | Melting Point | Analysis | | C | H | N | S | Cl |
|---|---|---|---|---|---|---|---|---|---|---|---|---|---|
| 1,3,5-triazino[2,1-b] benzothiazole | | | | | | | | | | | | | |
| 30 | S | 8-OCH$_3$ | 4-nitrophenyl | H | (a) Ex 1 | 260° | C$_{16}$H$_{12}$N$_6$O$_3$O | Found | 52.06 | 3.49 | 22.96 | 8.65% | |
| | | | | | | | | Reg. | 52.17 | 3.28 | 22.81 | 8.70% | |
| 2-Amino-8-methoxy-4-(4-nitrophenyl)imino 4H—1,3,5-triazino[2,1-b] benzothiazole | | | | | | | | | | | | | |

EXAMPLE 31

2-Amino-8-methoxy-4-methylimino-4H-1,3,5-triazino[2,1-b]benzothiazole (a)

N(Imino[(6-methoxybenzothiazol-2-yl)amino]methyl)-N'-methylthiourea

A mixture of the compound of Example 9(b) (0.5 g) and sodium hydride (0.054 g≡0.108 g of 50% dispersion in oil) in anhydrous dimethylformamide (20 ml) was stirred at room temperature for 15 min. Methyl isothiocyanate (0.16 g) was added and the mixture was stirred for a further 2 hrs. Water was added to the solution and the product extracted with ethyl acetate. The ethyl acetate solution was washed with water, dried over anhydrous sodium sulphate and evaporated to give a beige solid (0.67 g). Recrystallisation of the residue from ethanol/charcoal gave the sub-title product as pale yellow crystals (0.33 g), m.p. 197°–197.5°.

The Mass Spectrum showed M+295 (Mw295)

Found: C 45.07%; H 4.46%; N 23.75%; S 21.4%, C$_{11}$H$_{13}$N$_5$OS$_2$

Requires: C 44.73%; H 4.44%; N 23.71%, S 21.7%.

(b)

2-Amino-8-methoxy-4-methylimino-4H-1,3,5-triazino[2,1-b]-benzothiazole

A mixture of the product from step (a) (0.18 g) and sodium hydride (0.015 g≡0.03 g of 50% dispersion in oil) in anhydrous dimethylformamide was stirred at room temperature for 15 min. Methyl iodide (0.09 g was added and the resulting mixture stirred for a further 5 hr. Water was added to the solution and the product extracted with ethyl acetate. The ethyl acetate solution was washed with water, dried over anhydrous sodium sulphate and evaporated to give a yellow solid. Recrystallisation of the residue from ethyl acetate/charcoal gave the required product as white crystals (0.05 g) m.p. 208°–209°.

The Mass Spectrum showed M+261 (Mw 261).

Found: C50.48%; H4.38%; N27.05%; S12.26%, C$_{11}$H$_{11}$N$_5$OS

Requires: C50.56%; H4.24%; N26.80%; S12.27%.

EXAMPLE A

The compound of Example 1 has been shown to inhibit a delayed contact sensitivity to oxazolone in mice. This response is a measure of a cell-mediated immune response which is dependent on the activity of thymus-derived lymphocytes. Mice are sensitised with 100 μl of oxazolone and are subsequently challenged with 15 μl of 3% oxazolone on their right ears on day 7. The resulting cell-mediated response is measured 24 hours after challenge by assessing the increase of ear thickness using a dial gauge. The unchallenged left ears act as controls.

Mice receiving a single dose of the compound of Example 1 at 50 mg/kg by the intraperitoneal route, on one of the following days in relation to sensitisation; −1, 0, 1, 2, 3 or 7 show an inhibition of increased ear thickness.

Activity was most pronounced when the compound was dosed on days 1, 2, 3 and 7 when inhibition of 44, 44, 49 and 61% respectively was observed.

EXAMPLE B

The compound of Example 1 has been shown to suppress the rejection of skin grafts in mice. The tailskin grafting method of Bailey and Usania (Transplantation Bulletin 7, 424–5, 1960) was used.

Sections of tailskin from donor CBA strain mice (agonti) were grafted onto the tails of 16 Lac/a strain mice (albino). Test compound was given from 2 days prior to grafting until graft loss at a dose of 50 mg/kg/day in 1% "Tween 80"/saline vehicle by the intraperitoneal route. Graft condition was assessed daily and mean graft survival time (days) of vehicle, and drug tested groups, was compared.

The compound of Example 1 caused a significant prolongation (2.5 days) of skin graft survival.

TABLE

| | Mean Graft Survival Time |
|---|---|
| Vehicle Control | 11.8 ± 0.25* days |
| Compound of Ex 1 | 14.3 ± 0.65 days |

*Standard errors

EXAMPLE C

Delayed hypersensitivity in guinea pigs

The compound of Example 1 has been shown to suppress a delayed hypersensitivity reaction in guinea pigs when dosed topically. Male guinea pigs weighing 250–300 g were sensitised by a subcutaneous injection of Freunds Complete Adjuvant (Difco) in saline. Fourteen days following sensitisation animals were challenged intradermally into a shaved flank with 50 μg of purified protein derivative PPD (in 0.1 ml of saline). Changes in skin thickness were determined immediately before and 24 h and 48 h after antigen challenge. In addition, the diameter of reaction and a semiquantitative estimate of the degree of erythema were determined at 24 h and 48 h.

The compound of Example 1 was applied topically under an occlusive dressing. This consisted of adding a solution of the compound in dimethylacetamide (0.3 ml) to a filter paper square (4×4 cm) backed by surgical tape placed on the challenge site and held in place by adhesive bandage encircling the torso of the animal.

The dressing was applied 10 min after challenge and removed 24 h later. Control animals received dimethylacetamide alone to the challenge site.

Results

The effect of the compound of Example 1 applied under occlusion, with antigen challenge, on the delayed hypersensitivity reaction to PPD in guinea pigs (n=6)

| The compound of Example 1 conc. in dimethylacetamide | % Inhibition 24h after challenge | | |
|---|---|---|---|
| | Increase in skin thickness | Diameter of erythema | Erythema score |
| 1% | 20 | 5 | 20 |
| 2% | 35 | 16 | 32 |
| 3% | 50 | 34 | 63 |

The compound, at concentrations between 1 and 3% in dimethylacetamide caused a dose dependent inhibition of the increase in skin thickness at 24 hours post challenge and also significantly reduced the reaction diameters and erythema scores compared with controls treated with dimethylacetamide only. An inhibition of 20% or more was significant for all parameters.

EXAMPLE W

| Colloidal silica | 0.13% |
|---|---|
| Liquid paraffin | 4.05% |
| White soft paraffin | 40.52% |
| "Miglyol 812" | 2.59% |
| Glyceryl monostearate | 3.89% |
| Cetostearyl alcohol | 11.66% |
| Water | 21.94% |
| Propylene glycol | 13.72% |
| Compound of formula I (e.g. of Example 1) | 1.50% |
| | 100.00 |

We claim:

1. A compound of formula I,

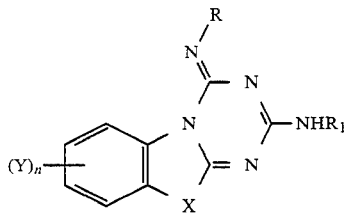

in which

X is O, S or N—$R_7$, each Y, which may be the same or different, is H, OH, alkyl C1–C8, alkoxy C1–C8 or halogen, n is an integer from 1 to 4 inclusive, R and $R_1$, which may be the same or different, are each H; alkanoyl C2–C8 or a group $R_4$ in which $R_4$ is alkyl C1–C8 optionally substituted by phenyl; or is cycloalkyl C5 or C6; or is a group of formula XVI,

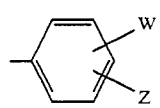

in which

W and Z, which may be the same or different, are each H, OH, alkoxy C1–C8, phenyl-alkoxy C7 to C10, alkyl C1–C8, halogen, —$NR_2R_3$, —$COOR_2$, $NO_2$, alkanoyloxy C2–C8, or —$OCH_2CH_2NR_2R_3$, and $R_2$, $R_3$ and $R_7$, which may be the same or different, are each H or alkyl C1–C8, provided that when X is N—$R_7$ and R is H, then $R_1$ is not (a) H when any Y groups are H, alkyl C1–C8, alkoxy C1–C8 or halogen, or (b) unsubstituted phenyl when all Y groups are H, and pharmaceutically acceptable salts thereof.

2. A compound according to claim 1, wherein X is S, each Y group, when it contains carbon, contains up to and including 4 carbon atoms, n is 1 or 2, R is hydrogen, phenyl, butyl, methyl, benzyloxyphenyl, benzyl, dimethylaminophenyl, mono- or di-halo-phenyl, methoxyphenyl, methylphenyl, carboxyphenyl, ethoxycarbonylphenyl, cyclohexyl, diethylaminoethoxyphenyl or hydroxyphenyl.

3. A compound according to claim 1, wherein R comprises a phenyl group.

4. A compound according to claim 1, wherein X is S, Y is alkoxy C1 to 4, n is 1, $R_1$ is hydrogen and R is phenyl optionally substituted by one or two chlorine atoms or by one group —$OCH_2CH_2N(C_2H_5)_2$.

5. A compound according to claim 4, wherein Y is methoxy in the 8-position and R is phenyl, 4-chlorophenyl, 3,4-dichlorophenyl or 4-(2-diethylaminoethoxy)-phenyl.

6. A compound according to claim 1, which is 2-Amino-8-methoxy-4-phenylimino-4H-1,3,5-triazino[2,1-b]benzothiazole or a pharmaceutically acceptable acid addition salt thereof.

7. A compound according to claim 1 which is 2-amino-4-phenylimino-4H-1,3,5-triazino[2,1-b]benzothiazole, or a pharmaceutically acceptable salt thereof.

8. A compound according to claim 1 which is 2-amino-4-phenylimino-4H-1,3,5-triazino[1,2-a]benzimidazole, or a pharmaceutically acceptable salt thereof.

9. A compound according to claim 1 which is 2-amino-8-methoxy-4-cyclohexylimino-4H-1,3,5-triazino[2,1-b]benzothiazole, or a pharmaceutically acceptable salt thereof.

10. A compound according to claim 1 which is 4-imino-8-methoxy-2-phenylamino-4H-1,3,5-triazino[2,1-b]benzothiazole, or a pharmaceutically acceptable salt thereof.

11. A compound according to claim 1 which is 2-acetylamino-8-methoxy-4-phenylimino-4H-1,3,5-triazino[2,1-b]benzothiazole, or a pharmaceutically acceptable salt thereof.

12. A compound according to claim 1 which is 2-amino-4-[4-(2-diethylaminoethoxy)phenyl]imino-8-methoxy-4H-1,3,5-triazino[2,1-b]benzothiazole, or a pharmaceutically acceptable salt thereof.

13. A compound according to claim 1 which is 8-methoxy-2-phenylamino-4-phenylimino-4H-1,3,5-triazino[2,1-b]benzothiazole or a pharmaceutically acceptable salt thereof.

14. A compound according to claim 1 which is 2-amino-4-(4-hydroxyphenyl)imino-8-methoxy-4H-1,3,5-triazino[2,1-b]benzothiazole, or a pharmaceutically acceptable salt thereof.

15. A compound according to claim 1 which is 2-amino-4-imino-4H-1,3,5-triazino[2,1-b]benzothiazole, or a pharmaceutically acceptable salt thereof.

16. A compound according to claim 1 which is 2-amino-8-methyl-4-phenylimino-4H-1,3,5-triazino[2,1- b]benzothiazole, or a pharmaceutically acceptable salt thereof.

17. A compound according to claim 1 which is 2-amino-4-(1,1-dimethylethyl)imino-8-methoxy-4H-1,3,5-triazino[2,1-b]benzothiazole, or a pharmaceutically acceptable salt thereof.

18. A compound according to claim 1 which is 2-amino-8-methoxy-4-[(phenylmethoxy)phenyl]imino-4H-1,3,5-triazino[2,1-b]benzothiazole, or a pharmaceutically acceptable salt thereof.

19. A compound according to claim 1 which is 2-amino-8-methoxy-4-phenylmethylimino-4H-1,3,5-triazino[2,1-b]benzothiazole, or a pharmaceutically acceptable salt thereof.

20. A compound according to claim 1 which is 2-amino-4-[4-(N,N-dimethylamino)phenyl]imino-8-methoxy-4H-1,3,5-triazino-[2,1-b]benzothiazole, or a pharmaceutically acceptable salt thereof.

21. A compound according to claim 1 which is 2-amino-8-(1-methylethoxy)-4-phenylimino-4H-1,3,5-triazino[2,1-b]benzothiazole, or a pharmaceutically acceptable salt thereof.

22. A compound according to claim 1 which is 2-amino-8-hydroxy-4-phenylimino-4H-1,3,5-triazino[2,1-b]benzothiazole, or a pharmaceutically acceptable salt thereof.

23. A compound according to claim 1 which is 2-amino-4-(2,6-dichlorophenyl)imino-8-methoxy-4H-1,3,5-triazino[2,1-b]benzothiazole, or a pharmaceutically acceptable salt thereof.

24. A compound according to claim 1 which is 2-amino-8-methoxy-4-(4-methoxyphenyl)imino-4H-1,3,5-triazino[2,1-b]benzothiazole, or a pharmaceutically acceptable salt thereof.

25. A compound according to claim 1 which is 2-amino-4-(3,4-dichlorophenyl)imino-8-methoxy-4H-1,3,5-triazino[2,1-b]benzothiazole, or a pharmaceutically acceptable salt thereof.

26. A compound according to claim 1 which is 2-amino-4-(4-chlorophenyl)imino-8-methoxy-4H-1,3,5-triazino[2,1-b]benzothiazole, or a pharmaceutically acceptable salt thereof.

27. A compound according to claim 1 which is 2-amino-8-methoxy-4-(4-methylphenyl)imino-4H-1,3,5-triazino[2,1-b]benzothiazole, or a pharmaceutically acceptable salt thereof.

28. A compound according to claim 1 which is 2-amino-4-phenylimino-4H-1,3,5-triazino[2,1-b]benzothiazole, or a pharmaceutically acceptable salt thereof.

29. A compound according to claim 1 which is 2-amino-8-chloro-4-phenylimino-4H-1,3,5-triazino[2,1-b]benzothiazole, or a pharmaceutically acceptable salt thereof.

30. A compound according to claim 1 which is 2-amino-4-(4-carboxylphenyl)imino-8-methoxy-4H-1,3,5-triazino[2,1-b]benzothiazole, or a pharmaceutically acceptable salt thereof.

31. A compound according to claim 1 which is 2-amino-4-(4-ethoxycarbonylphenyl)imino-8-methoxy-4H-1,3,5-triazino[2,1-b]benzothiazole, or a pharmaceutically acceptable salt thereof.

32. A compound according to claim 1 which is 2-amino-7,8-dimethyl-4-phenylimino-4H-1,3,5-triazino[2,1-b]benzothiazole, or a pharmaceutically acceptable salt thereof.

33. A compound according to claim 1 which is 2-amino-8-methoxy-4-(4-nitrophenylimino)-4H-1,3,5-triazino[2,1-b]benzothiazole, or a pharmaceutically acceptable salt thereof.

34. A compound according to claim 1 which is 2-amino-8-methoxy-4-methylimino-4H-1,3,5-triazino[2,1-b]benzothiazole, or a pharmaceutically acceptable salt thereof.

* * * * *